United States Patent
Max et al.

(10) Patent No.: US 10,736,832 B2
(45) Date of Patent: Aug. 11, 2020

(54) AQUEOUS SURFACTANT COMPOSITIONS

(71) Applicant: BASF SE, Ludwigshafen (DE)

(72) Inventors: Eva Max, Bayreuth (DE); Ansgar Behler, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/052,222

(22) Filed: Aug. 1, 2018

(65) Prior Publication Data

US 2018/0338898 A1 Nov. 29, 2018

Related U.S. Application Data

(63) Continuation of application No. 15/115,704, filed as application No. PCT/EP2015/051333 on Jan. 23, 2015.

(30) Foreign Application Priority Data

Feb. 4, 2014 (EP) ..................................... 14153833

(51) Int. Cl.
- A61K 8/60 (2006.01)
- A61K 8/46 (2006.01)
- A61Q 5/02 (2006.01)
- A61Q 9/02 (2006.01)
- A61Q 19/10 (2006.01)
- C11D 1/83 (2006.01)
- C11D 1/28 (2006.01)
- C11D 1/66 (2006.01)

(52) U.S. Cl.
CPC .............. *A61K 8/604* (2013.01); *A61K 8/466* (2013.01); *A61Q 5/02* (2013.01); *A61Q 9/02* (2013.01); *A61Q 19/10* (2013.01); *C11D 1/28* (2013.01); *C11D 1/662* (2013.01); *C11D 1/83* (2013.01); *A61K 2800/20* (2013.01)

(58) Field of Classification Search
CPC .. C11D 1/28; C11D 1/662; C11D 1/83; A61Q 5/02; A61Q 19/10; A61Q 9/02; A61K 8/604; A61K 8/466; A61K 2800/20
USPC ........................................................ 424/401
See application file for complete search history.

(56) References Cited

U.S. PATENT DOCUMENTS

| | | |
|---|---|---|
| 5,200,115 A | 4/1993 | Giesen et al. |
| 5,591,377 A | 1/1997 | Nickel et al. |
| 5,965,508 A * | 10/1999 | Ospinal ............... C11D 17/0065 510/152 |
| 2005/0153853 A1 | 7/2005 | Sajic et al. |
| 2009/0227482 A1 | 9/2009 | Dong et al. |
| 2012/0208898 A1* | 8/2012 | Dong ....................... A61K 8/20 514/785 |

FOREIGN PATENT DOCUMENTS

| | | |
|---|---|---|
| CN | 102686715 A | 9/2012 |
| DE | 3827778 A1 | 2/1990 |
| DE | 102007038029 A1 | 2/2009 |
| EP | 0070074 A2 * | 1/1983 |
| EP | 0070074 A2 | 1/1983 |

OTHER PUBLICATIONS

Definition of the word "Optional" from the Internet at: <http://www.dictionary.com/browse/optional>, downloaded Mar. 22, 2018.
International Search Report in International Patent Application No. PCT/EP2015/051333, dated May 21, 2015.
von Rybinski et al., Alkyl Polyglycosides-Properties and Applications of a new Class of Surfactants, Angew. Chem. Int. Ed. Engl., 37(10):1328-45 (Jun. 1998).

* cited by examiner

Primary Examiner — Yanzhi Zhang
(74) Attorney, Agent, or Firm — Marshall, Gerstein & Borun LLP

(57) ABSTRACT

An aqueous surfactant composition containing
  one or more alpha-sulfo fatty acid disalts (A) of the general formula (I),

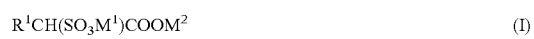

$$R^1CH(SO_3M^1)COOM^2 \quad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamine,
  one or more alkyl glycosides (B) of the general formula (II),

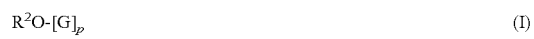

$$R^2O\text{-}[G]_p \quad (I)$$

in which $R^2$ is an alkyl and/or alkenyl radical with 8 to 18 carbon atoms, G is a sugar radical with 5 or 6 carbon atoms and p is numbers between 1 and 10,
  and water are disclosed. The composition has excellent foaming ability and is suitable for use in cosmetic products.

10 Claims, No Drawings

AQUEOUS SURFACTANT COMPOSITIONS

CROSS-REFERENCE TO RELATED APPLICATIONS

This is a continuation of U.S. patent application Ser. No. 15/115,704, filed Aug. 1, 2016, which is the U.S. national phase of International Patent Application No. PCT/EP2015/051333, filed Jan. 23, 2015, which claims the benefit of European Patent Application No. 14153833.0, filed Feb. 4, 2014.

FIELD OF THE INVENTION

The present invention relates to aqueous surfactant compositions with a content of alpha-sulfo fatty acid disalts and specific alkyl or alkenyl oligoglycosides.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. Furthermore, an adequate solubility in water, good compatibility with as many as possible of the active ingredients and auxiliaries used in cosmetics, a good foaming ability and good thickenability are generally desired. Furthermore, there is a need for anionic surfactants which can be produced at least partially from biogenic sources and specifically also renewable raw materials. Furthermore, there is also a need for surfactants which have no alkoxylated groups and which thus render superfluous in particular the use of ethylene oxide for their production.

DE-A-38,27,778 describes paste-like detergents and cleaners. Here, aqueous pastes are used which comprise an alkyl glucoside and an alpha-sulfo fatty acid disalt. Preference is given here to combinations of a $C_{12/14}$-alkyl glucoside with an alpha-sulfo fatty acid disalt based on $C_{16/18}$-fatty acid (tallow fatty acid), see for example column 3, lines 12-19 and example 1. As intended use, the document specifically specifies detergents and cleaners, column 5, lines 16-22 revealing that it concerns the manual cleaning of objects with hard surfaces, such as dishes, and the washing of textiles by hand or in a washing machine.

DESCRIPTION OF THE INVENTION

The object of the present invention was to provide aqueous surfactant compositions with a content of alkyl or alkenyl oligoglycosides which are characterized by an excellent foaming ability, in particular initial foaming behavior. The initial foaming behavior plays a very important role for so-called rinse-off products, which are to be understood as meaning products which come into contact with the skin during cleaning or grooming, but are then washed off again (e.g. shower gels, shower formulations, shampoos, liquid soaps, etc.). In this sector, as large a foam volume as possible is desired.

The aqueous surfactant compositions should moreover have hydrolysis stability both in the acidic and in the alkaline pH range and be as free as possible from constituents which comprise ethylene or propylene oxide building blocks or sulfate groups.

Furthermore, the aqueous surfactant compositions should either be able to be readily thickened to an adequately high viscosity or already by themselves have an adequately high viscosity. In the context of the present invention, adequately high viscosity is understood as meaning a value of 1000 mPas or higher and in particular a value in the range from 2000 to 8000 mPas (measured using a Brookfield RV laboratory rheometer at 20° C., 12 rpm, spindle set RV 02 to 07 (spindle choice depending on viscosity range)). As is known, "mPas" means millipascal seconds.

The aqueous surfactant compositions should also have a storage stability at room temperature (23° C.) of more than at least 8 weeks without any kind of visible changes (for example clouding, phase separations and the like) occurring and without viscosity changes or changes in the chemical composition arising.

The invention firstly provides aqueous surfactant compositions comprising one or more alpha-sulfo fatty acid disalts (A) of the general formula (I), $$R^1CH(SO_3M^1)COOM^2 \quad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamines, one or more alkyl glycosides (B) of the general formula (II), $$R^2O\text{-}[G]_p \quad (I)$$

in which $R^2$ is an alkyl and/or alkenyl radical with 8 to 18 carbon atoms, G is a sugar radical with 5 or 6 carbon atoms and p is numbers between 1 and 10, water, where the following provisos apply:

with regard to the compounds (A), it is the case that the fraction of the compounds (A) in which the radical $R^1$ is an alkyl or alkenyl radical with 14 or more carbon atoms—based on the total amount of the compounds (A) in the aqueous surfactant compositions—is 20% by weight or less;

with regard to the compounds (B), it is the case that the fraction of the compounds (B) in which the radical $R^2$ is an alkyl or alkenyl radical with 15 or more carbon atoms—based on the total amount of the compounds (B) in the aqueous surfactant compositions—is 5% by weight or less;

if the aqueous surfactant compositions comprise one or more ester sulfonates (E) of the general formula (V), $$R^5CH(SO_3M^5)COOR^6 \quad (V)$$

in which the radical $R^5$ is a linear or branched alkyl or alkenyl radical with 6 to 18 carbon atoms and the radical $R^6$ is a linear or branched alkyl or alkenyl radical with 1 to 20 carbon atoms, where the radical $R^6$ can logically be an alkenyl radical or be branched only above 3 carbon atoms, and the radical $M^5$ is selected from the group Li, Na, K, Ca/2, Mg/2, ammonium and alkanolamines, it is the case that the compounds (A)—based on the totality of the compounds (A) and (E)—must be present to 50% by weight or more—and in particular to 90% by weight or more;

the weight ratio of the compounds (A):(B) in the aqueous surfactant compositions is in the range from 0.6:1 to 1:0.6.

The Compounds (A)

The compounds (A), which are referred to within the context of the present invention as alpha-sulfo fatty acid disalts, are obligatory for the aqueous surfactant compositions according to the invention. They have the aforementioned formula (I)

$$R^1CH(SO_3M^1)COOM^2 \quad (I)$$

in which the radical $R^1$ is a linear or branched alkyl or alkenyl radical with 6 to 16 carbon atoms and the radicals $M^1$ and $M^2$—independently of one another—are selected from the group H, Li, Na, K, Ca/2, Mg/2, ammonium and alkanolamines. With regard to the compounds (A), the proviso also applies that the fraction of the compounds (A) in which the radical $R^1$ is an alkyl or alkenyl radical with 14 or more carbon atoms—based on the total amount of the compounds (A) in the aqueous surfactant compositions—is 20% by weight or less.

In one embodiment, the proviso applies that the fraction of the compounds (A) in the aqueous surfactant compositions in which the radical $R^1$ is an alkenyl radical—based on the total amount of the compounds (A)—is 3% by weight or less.

In a preferred embodiment, the radical $R^1$ in the formula (I) means a saturated, linear radical with 10 to 16 carbon atoms, where, with regard to the compounds (A), it is the case that the fraction of the compounds (A) in which the radical $R^1$ is a decyl and/or a dodecyl radical—based on the total amount of the compounds (A)—is 90% by weight or more.

Preferably, the radicals $M^1$ and $M^2$ in the formula (I) are Na.

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

Within the context of the present invention, preference is given to those technical-grade mixtures of the alpha-sulfo fatty acid disalts which have the following composition:

the content of (A) is in the range from 60 to 100% by weight, the content of (C) is in the range from 0 to 20% by weight, the content of (D) is in the range from 0 to 20% by weight, with the proviso that the sum of the components (A), (C) and (D) in this mixture is 100% by weight.

Very particular preference is given to those technical-grade mixtures at have the composition as follows:

the content of (A) is in the range from 70 to 80% by weight, the content of (C) is in the range from 10 to 15% by weight, the content of (D) is in the range from 10 to 15% by weight, with the proviso that the sum of the components (A), (C) and (D) in this mixture is 100% by weight.

The Compounds (B)

The compounds (B), which are referred to in the context of the present invention as alkyl glycosides, are obligatory for the aqueous surfactant compositions according to the invention. They have the aforementioned formula (II),

$$R^2O\text{-}[G]_p \quad (I)$$

in which $R^2$ is an alkyl and/or alkenyl radical with 8 to 18 carbon atoms, G is a sugar radical with 5 or 6 carbon atoms and p is numbers between 1 and 10. With regard to the compounds (B), the proviso also applies that the fraction of the compounds (B) in which the radical $R^2$ is an alkyl or alkenyl radical with 15 or more carbon atoms—based on the total amount of the compounds (B) in the aqueous surfactant compositions—is 5% by weight or less.

It may expressly be stated that the naming of the compounds (B) as alkyl glycosides—henceforth also referred to as APGs (singular: APG)—serves merely for a linguistically simple naming of the compounds (B) and should not be understood as being structurally limiting; hence in the definition according to the formula of the compounds (B) it is clarified that the radical $R^2$ can mean either an alkyl or an alkenyl radical and also—as the index p shows—that they can be alkyl or alkenyl oligoglycosides.

APGs of the form claimed here can be obtained by the relevant methods of preparative organic chemistry. The APGs can be derived from aldoses or ketoses with 5 or 6 carbon atoms. Preferably, the APGs are derived from glucose.

The index number p in the general formula (I) indicates the degree of oligomerization (DP degree=degree of polymerization). The degree of oligomerization of the APGs is between 1 and 10 and preferably between 1 and 6. Whereas p in an individual APG molecule must always be an integer and here in particular assumes the values in the range from 1 to 6, the value p for an APG which is a mixture of different APG molecules, which differ in their individual p values, is an analytically determined calculated parameter which in most cases is a fraction. Preferably, APGs are used with an average degree of oligomerization p in the range from 1.1 to 3.0. In this connection, preference is given in particular to those APGs whose average degree of oligomerization is less than 2 and is preferably in the range from 1.1 to 1.8 and in particular in the range from 1.2 to 1.7.

The average degree of oligomerization here is to be understood in the sense of how it is defined in the monograph K. Hill, W. von Rybinski, G. Stoll "Alkyl Polyglycosides. Technology, Properties and Applications" (VCH-Verlagsgesellschft, 1996) in the section "Degree of polymerization" (compare pages 11-12 of the book): there it reads "The average number of glycose units linked to an alcohol group is described as the (average) degree of polymerization (DP)." In explanatory FIG. 2, which describes a typical distribution of dodecyl glycoside oligomers of an AOPG with a degree of DP of 1.3, the average degree of DP is also described by a corresponding mathematical formula.

The radical $R^2$ is preferably derived from primary alcohols with 4 to 11 carbon atoms and preferably 8 to 10 carbon atoms. Typical examples of suitable radicals $R^2$ are butyl, hexyl, octyl, decyl, undecyl, dodecyl and myristyl. They are derived from the saturated fatty alcohols butanol-1, caproic alcohol (hexanol-1), caprylic alcohol (octanol-1), capric alcohol (decanol-1), undecanol-1, lauryl alcohol (dodecanol-1) and myristyl alcohol (tetradecanol-1), as are obtained for example in the hydrogenation of technical-grade fatty acid methyl esters or in the course of the hydrogenation of aldehydes during Roelen oxo synthesis.

Preference is given to APGs which are derived from glucose and in which the radical $R^2$ is a saturated alkyl radical with 8 to 12 carbon atoms and which have an average degree of oligomerization in the range from 1.1 to 3 and in particular in the range from 1.2 to 1.8 and particularly preferably in the range from 1.2 to 1.7. These APGs can for example be prepared by reacting a sugar, in particular glucose, under acid catalysis with a fatty alcohol mixture, the fatty acid mixture used preferably being a forerunning produced during the distillative separation of technical-grade $C_{8-18}$-coconut fatty alcohol, which comprises predominantly octanol-1 and decanol-1 and also small amounts of dodecanol-1.

PREFERRED EMBODIMENTS

In one embodiment, the aqueous surfactant compositions according to the invention comprise, besides the compounds (A), (B) and water, additionally one or more compounds (C) of the general formula (III)

$$R^4COOM^3 \qquad (III)$$

In the formula (III), the radical $R^4$ is a linear or branched alkyl or alkenyl radical with 7 to 17 carbon atoms and the radicals $M^3$ is selected from the group H, Li, Na, K, Ca/2, Mg/2, ammonium and alkanolamines.

In one embodiment, the aqueous surfactant compositions according to the invention comprise, besides the compounds (A), (B) and water, additionally one or more inorganic salts of sulfuric acid (D) of the general formula (IV)

$$(M^4)_2SO_4 \qquad (IV)$$

where $M^4$ is selected from the group Li, Na, K, Ca/2, Mg/2, ammonium and alkanolamine.

The radicals $M^1$ and $M^2$ of the compounds (A), the radical $M^3$ of the compounds (C) and the radical $M^4$ of the compounds (D) can be alkanolamines. In this connection, particular preference is given to monoethanolamine, diethanolamine, triethanolamine and monoisopropanolamine.

In a preferred embodiment, the aqueous surfactant compositions according to the invention comprise the compounds (A), (B), (C) and (D). Here, it is particularly preferred if $M^1$ and $M^2$ of the compounds (A), the radical $M^3$ of the compounds (C) and the radical $M^4$ of the compounds (D) has the meaning Na (sodium).

In one embodiment, the content of the compounds (A) and (B) in the compositions—based on the total composition—is at least 1% by weight. Preferably, the content of the compounds (A) and (B) in the compositions—based on the total composition—is in the range from 5 to 50% by weight, in particular in the range from 5 to 20% by weight and particularly preferably in the range from 8 to 12% by weight.

As stated above, the weight ratio of the compounds (A):(B) in the aqueous surfactant compositions is in the range from 0.6:1 to 1:0.6. Preferably, the weight ratio of the compounds (A):(B) in the aqueous surfactant compositions is in the range from 0.7:1 to 1:0.7, and especially in the range from 0.8:1 to 1:0.8. The range from 0.9:1 to 1:0.9 is very particularly preferred.

In one embodiment, the pH of the compositions is in the range from 4.3 to 5.8.

The viscosity of the aqueous surfactant compositions—measured using a Brookfield RV laboratory rheometer at 20° C., 12 rpm, spindle set RV 02 to 07 (spindle choice depending on viscosity range)—is preferably 1000 mPas or higher.

If desired, the aqueous surfactant compositions according to the invention can additionally comprise one or more further surfactants which, in structural terms, do not belong to the aforementioned compounds (A), (B), (D) or (E). These surfactants may be anionic, cationic, nonionic or amphoteric surfactants.

Use of the Compositions

A further subject matter of the invention is the use of the aforementioned compositions for cosmetic products.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

EXAMPLES

Substances Used

SFA-I: alpha-sulfo fatty acid disalt of technical grade based on native $C_{12/14}$-fatty acid; composition: 74% by weight disodium 2-sulfolaurate, 13% by weight sodium laurate, 11% by weight sodium sulfate, 2% by weight water. The term "laurate" here means that the C12/14 ratio of the mixture of the underlying native fatty acids is 70:30. Active substance content—based on disalt—74% by weight APG-I: Standard commercial $C_{12-C16}$-fatty alcohol glycoside, active substance content: 50-53% by weight, water fraction: 47-50% by weight, pH about 11.5-12.5 (Planatacare 1200 UP, BASF BPCN)

Measurement and Test Methods

Determination of the Initial Foaming Behavior:

To test the initial foaming behavior (rotor foam method), a standard commercial measuring instrument was used (Sita Foam Tester R 2000). For this, an aqueous surfactant solution was firstly prepared as follows: 1 g of active substance of each sample to be tested (the samples used were SFA-I or APG-I or mixtures of these substances, see below; in the case of SFA-I, active substance content is understood—as stated above—as meaning the disalt content) was dissolved at 20° C. in 1 liter of water with a degree of hardness of 15° German hardness (corresponds to 2.673 mmol of $CaCO_3$). The pH of the solution was adjusted to 5.5 with HCl. The solution prepared in this way was heated to 30° C.

Measurement: 250 ml of the heated reservoir were transferred to the measuring instrument and foamed at a speed of 1300 revolutions per minute for 10 seconds, the foam volume then present was ascertained (in ml), then foamed for a further 10 seconds, the foam volume then present was ascertained (in ml), etc., i.e. the foam level was determined every 10 seconds during foaming. After a foaming time of 80 seconds, the measurement was ended. The measurement was repeated for each sample 3 times, in each case using a fresh solution from the same batch, and the result of the measurements after 40, 60 and 80 seconds was given as an average from these three measurements (see table).

EXAMPLES

Example 1

A mixture of SFA-I and AGP-I was used, where the weight ratio of the respective active substance of SFA-I and AGP-I was adjusted to a value of 1:1. The experimental procedure was carried out as described above under "Determination of the initial foaming behavior". The experimental data can be found in Table 1.

Comparative Example 1

Exclusively SFA-I was used. The experimental procedure was carried out as described above under "Determination of the initial foaming behavior". The experimental data can be found in Table 1.

Comparative Example 2

Exclusively APG-I was used. The experimental procedure was carried out as described above under "Determination of the initial foaming behavior". The experimental data can be found in Table 1.

Comparative Example 3

A mixture of SFA-I and AGP-I was used, where the weight ratio of the respective active substance of SFA-I and AGP-I was adjusted to a value of 3:1. The experimental procedure was carried out as described above under "Determination of the initial foaming behavior". The experimental data can be found in Table 1.

Comparative Example 4

A mixture of SFA-I and AGP-I was used, where the weight ratio of the respective active substance of SFA-I and AGP-I was adjusted to a value of 1:3. The experimental procedure was carried out as described above under "Determination of the initial foaming behavior". The experimental data can be found in Table 1.

teaches that surprisingly a synergy of the foam behaviour is present. Comparatives examples 3 and 4 show that outside of the range according to the invention the mixture of the surfactants SFA-I and SFA-II exhibits poor foam behavior.

The invention claimed is:
1. An aqueous surfactant composition comprising
one or more alpha-sulfo fatty acid disalt (A) of general formula (I),

$$R^1CH(SO_3M^1)COOM^2 \quad (I)$$

in which radical $R^1$ is a linear or branched alkyl radical with 6 to 16 carbon atoms and the radicals $M^1$ and $M^2$, independently of one another, are selected from the group consisting of Li, Na, K, Ca/2, Mg/2, ammonium, and alkanolamine, one or more alkyl glycosides (B) of general formula (II), $$R^2O-[G]_p \quad (II),$$

in which $R^2$ is an alkyl radical with 8 to 18 carbon atoms, G is a sugar radical with 5 or 6 carbon atoms, and p is numbers between 1 and 10, optionally one or more ester sulfonate (E) of general formula (V), $$R^5CH(SO_3M^5)COOR^6 \quad (V),$$

in which radical $R^5$ is a linear or branched alkyl radical with 6 to 18 carbon atoms and radical $R^6$ is a linear or branched alkyl radical with 1 to 20 carbon atoms, and the radical $M^5$ is selected from the group consisting of Li, Na, K, Ca/2, Mg/2, ammonium, and alkanolamine, one or more compound (C) of general formula (III), $$R^4COOM^3 \quad (III),$$

in which the radical $R^4$ is a linear or branched alkyl or alkenyl radical with 7 to 19 carbon atoms and the radical $M^3$ is selected from the group consisting of H, Li, Na, K, Ca/2, Mg/2, ammonium, and alkanolamine, one or more inorganic salt of sulfuric acid (D) of general formula (IV), $$(M^4)_2SO_4 \quad (IV),$$

wherein $M^4$ is selected from the group consisting of Li, Na, K, Ca/2, Mg/2, ammonium, and alkanolamine, and water, wherein a pH of the composition is in a range of 4.3 to 5.8, where the following provisos apply:

TABLE 1

Determination of the initial foaming behavior

|  | Example 1 | Comparative example 1 | Comparative example 2 | Comparative example 3 | Comparative example 3 |
|---|---|---|---|---|---|
| SFA-I | 0.67 g | 1.35 g |  | 1.01 g | 0.34 g |
| APG-I | 0.96 g |  | 1.92 g | 0.48 g | 1.44 g |
| Ratio of SFA-I:APG-I | 1:1 | 1:0 | 0:1 | 3:1 | 1:3 |
| Foam volume after 40 sec | 430 ml | 148 ml | 333 ml | 278 ml | 173 ml |
| Foam volume after 60 sec | 618 ml | 188 ml | 433 ml | 358 ml | 235 ml |
| Foam volume after 80 sec | 868 ml | 215 ml | 519 ml | 446 ml | 292 ml |

It is clear from the table that the mixtures according to the invention (demonstrated by example 1) can be used to attain a quite excellent foam behavior. The comparison with comparative examples 1 and 2, in which only individual surfactants, i.e. only SFA-I or only APG-I, were used in each case, (a) with regard to the compound (A), it is the case that a fraction of the compound (A) in which the radical $R^1$ is an alkyl radical with 14 or more carbon atoms, based on the total amount of the compound (A) in the aqueous surfactant composition, is 20% by weight or less;

(b) with regard to the compound (B), it is the case that a fraction of the compound (B) in which the radical $R^2$ is an alkyl or alkenyl radical with 15 or more carbon atoms, based on the total amount of the compound (B) in the aqueous surfactant composition, is 5% by weight or less;

(c) when the aqueous surfactant composition comprises one or more optional ester sulfonate (E) of general formula (V), then it is the case that the compound (A), based on the totality of the compounds (A) and (E), is present at 90% by weight or more;

(d) a weight ratio of the compounds (A):(B) in the aqueous surfactant composition is in the range from 0.6:1 to 1:0.6; and (e) with regard to a mixture of components (A), (C), and (D), a content of (A) in the mixture of (A), (C), and (D) is in a range from 70 to 80% by weight, a content of (C) in the mixture of (A), (C), and (D) is in a range from 10 to 15% by weight, a content of (D) in the mixture of (A), (C), and (D) is in a range from 10 to 15% by weight, wherein a sum of (A), (C), and (D) in the mixture of (A), (C), and (D) is 100% by weight.

2. The composition according to claim 1, where the radicals $M^1$ and $M^2$ are Na.

3. The composition according to claim 1, wherein the weight ratio of compound (A):(B) in the composition is in a range of 0.7:1 to 1:0.7.

4. The composition according to claim 1, wherein the weight ratio of compound (A):(B) in the composition is in a range of 0.9:1 to 1:0.9.

5. The composition according to claim 1 wherein the alpha-sulfo fatty acid disalt (A) comprises disodium 2-sulfolaurate.

6. The composition according to claim 1 wherein the alkyl glycoside (B) has p numbers between 1 and 6.

7. The composition according to claim 6 wherein the alkyl glycoside (B) has an average p in a range of 1.1 to 3.0.

8. The composition according to claim 1 wherein $R^2$ of alkyl glycosides (B) is an alkyl radical with 8 to 12 carbon atoms.

9. A cosmetic product comprising a composition according claim 1.

10. The cosmetic product according to claim 9 in the form of hair shampoos, shower gels, soaps, syndets, washing pastes, washing lotions, scrub preparations, foam baths, oil baths, shower baths, shaving foams, shaving lotions, and shaving creams.

* * * * *